United States Patent
Wang et al.

(10) Patent No.: US 9,952,140 B2
(45) Date of Patent: Apr. 24, 2018

(54) SMALL SPOT SIZE SPECTROSCOPIC ELLIPSOMETER

(71) Applicant: KLA-Tencor Corporation, Milpitas, CA (US)

(72) Inventors: Haiming Wang, Fremont, CA (US); Shankar Krishnan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 172 days.

(21) Appl. No.: 13/903,070

(22) Filed: May 28, 2013

(65) Prior Publication Data
US 2013/0321810 A1    Dec. 5, 2013

Related U.S. Application Data

(60) Provisional application No. 61/652,769, filed on May 29, 2012.

(51) Int. Cl.
| | | |
|---|---|---|
| G01J 4/00 | (2006.01) | |
| G01N 21/21 | (2006.01) | |
| G03F 7/20 | (2006.01) | |

(52) U.S. Cl.
CPC ....... *G01N 21/211* (2013.01); *G03F 7/70625* (2013.01)

(58) Field of Classification Search
CPC . G01J 3/447; G01N 21/211; G01N 2021/213; G01N 2021/214; G03F 7/70625
See application file for complete search history.

(56) References Cited

U.S. PATENT DOCUMENTS

| | | |
|---|---|---|
| 5,042,951 A | 8/1991 | Gold et al. |
| 5,581,350 A | 12/1996 | Chen et al. |

(Continued)

FOREIGN PATENT DOCUMENTS

KR    1020080106892 A    12/2008

OTHER PUBLICATIONS

Holden, James M., et al. "Normal-incidence spectroscopic ellipsometry and polarized reflectometry for measurement and control of photoresist critical dimension." SPIE's 27th Annual International Symposium on Microlithography. International Society for Optics and Photonics, 2002.*

(Continued)

*Primary Examiner* — Tri Ton
*Assistant Examiner* — Rufus Phillips
(74) *Attorney, Agent, or Firm* — Spano Law Group; Joseph S. Spano

(57) ABSTRACT

Methods and systems for small angle CD metrology with a small spot size are introduced to increase measurement sensitivity while maintaining adequate throughput necessary for modern semiconductor manufacture. A small angle CD metrology system includes a small angle spectroscopic ellipsometry (SE) subsystem combined with a small angle spectroscopic reflectometry system, both operated at small angles of incidence. The small angle SE subsystem is configured to operate in a complete Mueller Matrix mode to further improve measurement sensitivity. The small angle CD metrology system includes an objective having all reflective surfaces in the light path. In some embodiments, the all-reflective objective is a Schwartzschild objective having an axicon mirror element to further reduce measurement spot size. In some embodiments, the small angle CD metrology system includes a dynamic aperture subsystem to (Continued)

isolate specific ranges of angles of incidence and azimuth for improved measurement sensitivity.

19 Claims, 7 Drawing Sheets

(56) References Cited

U.S. PATENT DOCUMENTS

| | | | |
|---|---|---|---|
| 5,608,526 A | 3/1997 | Piwonka-Corle et al. | |
| 5,798,837 A | 8/1998 | Aspnes et al. | |
| 6,191,846 B1* | 2/2001 | Opsal et al. | 356/72 |
| 6,483,580 B1* | 11/2002 | Xu et al. | 356/300 |
| 6,678,046 B2* | 1/2004 | Opsal | G01B 11/0641 356/369 |
| 6,734,968 B1 | 5/2004 | Wang et al. | |
| 6,778,273 B2* | 8/2004 | Norton et al. | 356/364 |
| 7,286,243 B2* | 10/2007 | Rosencwaig | G01B 11/0625 356/369 |
| 7,385,697 B2* | 6/2008 | Woollam | G01N 21/211 356/369 |
| 8,144,337 B2* | 3/2012 | Hamamatsu | G01B 11/303 356/600 |
| 8,553,219 B2* | 10/2013 | Patil | A61B 3/102 356/301 |
| 8,634,067 B2* | 1/2014 | Perelman | G02B 21/0052 356/337 |
| 8,908,167 B2* | 12/2014 | Flora | G02B 21/0016 356/237.1 |
| 2002/0008874 A1 | 1/2002 | Lee et al. | |
| 2004/0017561 A1* | 1/2004 | Meeks | 356/237.3 |
| 2004/0100632 A1* | 5/2004 | Piwonka-Corle | G01N 21/211 356/364 |
| 2004/0169861 A1* | 9/2004 | Mieher | G01N 21/956 356/400 |
| 2005/0006590 A1* | 1/2005 | Harrison | G01J 3/02 250/372 |
| 2005/0041250 A1* | 2/2005 | Opsal | G01B 11/0641 356/369 |
| 2007/0229852 A1 | 10/2007 | Wack et al. | |
| 2010/0177324 A1 | 7/2010 | Walsh | |
| 2011/0080585 A1 | 4/2011 | Rabello et al. | |
| 2011/0205529 A1* | 8/2011 | Gross et al. | 356/51 |
| 2013/0169954 A1* | 7/2013 | Gibson | G01J 3/02 356/72 |

OTHER PUBLICATIONS

Huang, Hsu-Ting, Wei Kong, and Fred Lewis Terry Jr. "Normal-incidence spectroscopic ellipsometry for critical dimension monitoring." Applied Physics Letters 78.25 (2001): 3983-3985.*

McGahan, William A., et al. "Combined spectroscopic ellipsometry and reflectometry for advanced semiconductor fabrication metrology." Microelectronic Manufacturing 1996. International Society for Optics and Photonics, 1996.*

Laskarakis, A., et al. "Mueller matrix spectroscopic ellipsometry: formulation and application." Thin Solid Films 455 (2004): 43-49.*

P.S. Hauge, "Mueller matrix ellipsometry with imperfect compensators", JOSA A 68(11), 1519-1528, 1978.

R.M.A Azzam, "A simple Fourier photopolarimeter with rotating polarizer and analyzer for measuring Jones and Mueller matrices", Opt Comm 25(2), 137-140, 1978.

M. L. Aleksandrov, et. al. "Methods and apparatus for complete ellipsometry (review)", J Appl Spectroscopy 44(6), 559-578, 1986.

International Search Report and Written Opinion dated Aug. 28, 2013, for PCT Application No. PCT/US2013/042900 filed on May 28, 2013, by KLA-Tencor Corporation, 3 pages.

* cited by examiner

SMALL SPOT SIZE SPECTROSCOPIC ELLIPSOMETER

CROSS REFERENCE TO RELATED APPLICATION

The present application for patent claims priority under 35 U.S.C. § 119 from U.S. provisional patent application Ser. No. 61/652,769, entitled "Small Spot Size, High Sensitivity, High Speed Mueller Matrix Spectroscopic Ellipsometric System and Method," filed May 29, 2012, the subject matter of which is incorporated herein by reference in its entirety.

TECHNICAL FIELD

The described embodiments relate to optical metrology systems and methods, and more particularly to methods and systems for improved precision across critical dimension measurement applications.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty.

Spectroscopic ellipsometry (SE) is commonly used to measure thin films, including the optical properties and thickness of film stacks. In general a SE system is based on the polarimetric principle. A light beam with a defined polarization state is directed to a sample. After interacting with the sample, the polarization state of the incident beam is modified. This modification of polarization state manifests itself as a change in the magnitude and phase of two orthogonally polarized components. For the case of linearly polarized light, the two orthogonally polarization components are commonly referred to as s- and p-polarization. In a semiconductor fabrication environment, ellipsometric measurements are typically performed on materials (e.g., silicon, silicon dioxide, silicon nitride, photoresist, etc.) that are optically isotropic. To obtain satisfactory measurement results it has been necessary to build SE systems with a relatively large angle of incidence (AOI) of the incident beam on the sample. For example, for a rotating compensator spectroscopic ellipsometer (RCSE) an AOI is typically set at 60 degrees and higher. In another example, for a rotating polarizer spectroscopic ellipsometer (RPSE) the AOI is typically set close to the Brewster's angle of silicon (i.e., approximately 70 degrees). For measurements of optically isotropic materials with typical RPSE and RCSE systems, selection of small angles of incidence results in substantially reduced measurement sensitivity.

As critical dimensions (e.g., the gate width or gate oxide thickness) continue to decrease, maintaining measurement precision (e.g., "3-sigma" measurement values) and tool-to-tool matching becomes progressively more difficult. As the values of the underlying structural parameters continue to shrink, the signal changes corresponding to a fractional change in the structural parameters become indistinguishable from system noise for typical RPSE or RCSE systems. As a result, both precision and tool-to-tool matching degrade.

Measurement precision and tool-to-tool matching are core challenges in the development of an optical metrology system that meets customer requirements of the semiconductor industry. Process and yield control in both the research and development and manufacturing environments demands increasing measurement precision and tool-to-tool consistency of measurement results. Thus, methods and systems for improved measurement sensitivity to meet the challenging CD and overlay metrology requirements are desired.

SUMMARY

A small angle CD metrology system with a small spot size is introduced to increase measurement sensitivity while maintaining adequate throughput necessary for modern semiconductor manufacture. As the size of CD measurement targets continue to shrink, the desired spot size also becomes smaller. The metrology system introduced herein is able to measure CD measurement targets with high sensitivity over a small spot size (e.g., a spot size of 15 microns in diameter, or less).

In one aspect, the small angle CD metrology system includes a small angle spectroscopic ellipsometry (SE) subsystem combined with a small angle spectroscopic reflectometry system, both operated at small angles of incidence. In a further aspect, the small angle SE subsystem is configured to operate in a complete Mueller Matrix mode to further improve measurement sensitivity.

In another aspect, the small angle CD metrology system includes an objective having all reflective surfaces in the light path. An all-reflective objective allows for a large numerical aperture, thus enabling high angular resolution. The all-reflective objective can be produced with minimal chromatic aberration and a high degree of mechanical stability. In some embodiments, the all-reflective objective is a Schwartzschild objective having an axicon mirror element to further reduce measurement spot size.

In yet another further aspect, measurements are performed by the small angle CD metrology system at two orthogonal, or nearly orthogonal azimuth angles to further improve measurement sensitivity.

In yet another further aspect, the small angle CD metrology system includes a dynamic aperture subsystem to enable measurements at different angles of incidence and different azimuth angles. The dynamic aperture subsystem is operable to isolate specific ranges of angles of incidence and azimuth for improved measurement sensitivity.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
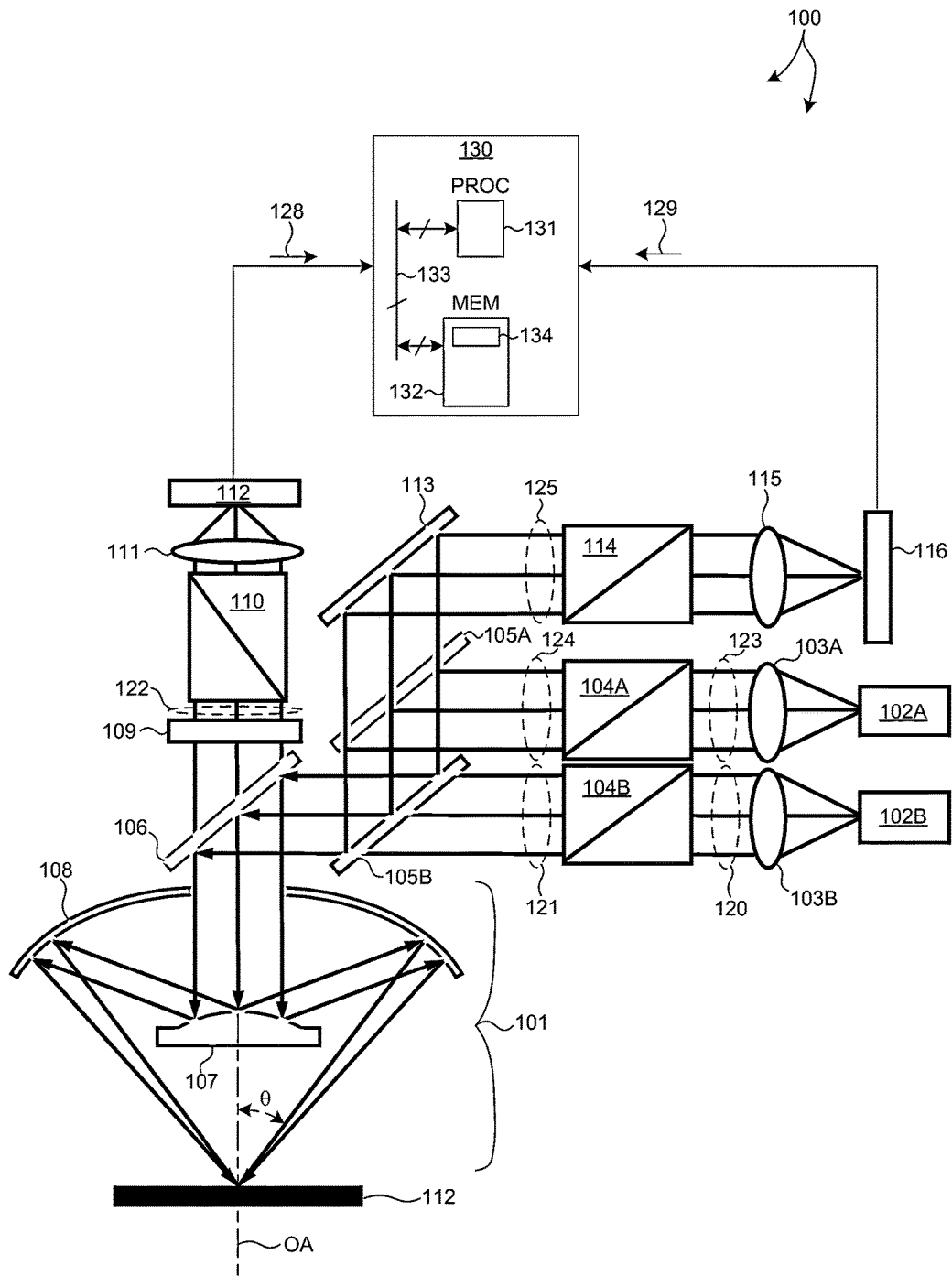
FIG. 1 is a diagram illustrative of a small angle CD metrology system 100 for measuring structural characteristics of a semiconductor wafer.

Reference will now be made in detail to background examples and some embodiments of the invention, examples of which are illustrated in the accompanying drawings.

Methods and systems for Critical Dimension (CD) measurement applications with high sensitivity and throughput requirements are presented. Such systems are employed to measure structural and material characteristics (e.g., material composition, dimensional characteristics of structures and films, etc.) associated with different semiconductor fabrication processes.

A small angle CD metrology system with a small spot size is introduced to increase measurement sensitivity while maintaining adequate throughput necessary for modern semiconductor manufacture. As the size of CD measurement targets continue to shrink, the desired spot size also becomes smaller. The system introduced herein is able to measure CD measurement targets with high sensitivity over a small spot size (e.g., a spot size of 15 microns in diameter, or less).

In one aspect, the small angle CD metrology system includes a small angle spectroscopic ellipsometry (SE) subsystem combined with a small angle spectroscopic reflectometry system, both operated at small angles of incidence, thus enabling a small spot size with high measurement sensitivity. The inventors have discovered that for sample structures that are optically anisotropic, it is not necessary to operate a spectroscopic ellipsometry (SE) system at large angles of incidence. For example, for a grating-like structure, the optical properties in the direction perpendicular to the grating lines are substantially different from those in the direction parallel to the grating lines. As a result, SE measurements performed at small angles of incidence are capable of yielding useful results, while enabling smaller spot sizes compared to traditional SE systems.

The small angle CD metrology system includes an objective having all reflective surfaces in the light path. An all-reflective objective allows for a large numerical aperture, thus enabling high angular resolution. The all-reflective objective having a large numerical aperture also enables several other aspects of the novel, small angle CD metrology system. In some embodiments, the large numerical aperture enables the small angle SE system to operate in a complete Mueller Matrix mode. In some embodiments, the large numerical aperture enables the small angle SE system to operate in combination with a spectroscopic reflectometer (SR) system. In some embodiments, the large numerical aperture enables the small angle SE system to include dynamic aperture selection functionality to perform measurements with high angular resolution. Moreover, all-reflective objectives can be produced with minimal chromatic aberration and a high degree of mechanical stability. Although embodiments of the small angle CD metrology system including an all-reflective objective are presented herein, other embodiments may be contemplated that include transmissive elements.

FIG. 1 illustrates a schematic view of an exemplary embodiment of a small angle CD metrology system 100 for measuring structural characteristics of a semiconductor wafer. As shown in FIG. 1, system 100 is configured to perform spectroscopic ellipsometry measurements of one or more structures of a semiconductor wafer 112 disposed on a wafer positioning system (not shown). System 100 includes at least one broadband illumination source. The illumination source is configured to generate illumination light of a selected wavelength range (e.g., 150-2000 nm) that is directed to the surface of the semiconductor wafer 112. The broadband illumination source preferably generates light with a spectral range extending from vacuum ultraviolet (VUV), or approximately 150 nm, up to infrared (IR), or above 2,000 nm. By way of non-limiting example, the optical illumination source includes one or more arc lamps, halogen lamps, lasers, light emitting diodes, laser driven plasma sources, and laser driven supercontinuum sources, or any combination thereof. In general, any suitable optical illumination source capable of producing illumination in the visible, infrared, and ultraviolet spectral ranges may be contemplated. Moreover, it is contemplated herein that two or more broadband illumination sources may be combined to achieve a desired broadband spectral range. In the depicted embodiment, system 100 includes two illumination sources 102A and 102B. Illumination source 102A is a xenon lamp capable of delivering light in a spectral range of 190 nm to 2000 nm, with a gradual radiant intensity decrease below 400 nm. Illumination source 102B is a deuterium arc lamp capable of delivering light with a continuous spectrum below 400 nm, with a gradual radiant intensity decrease below 250 nm. In yet another embodiment, a single, laser-driven plasma light source is employed to generate the desired broadband spectral range.

The embodiment of small angle CD metrology system 100 depicted in FIG. 1 includes a rotating polarizer, rotating compensator spectroscopic ellipsometer (RPRC SE) subsystem configured to perform SE measurements over small angles of incidence. The RPRC SE subsystem includes polarizer 104B, objective 101, compensator 109, analyzer 110, and spectrometer 112.

As depicted in FIG. 1, a light beam from illumination source 102B is collimated by beam forming optics 103B to generate an illumination light beam 120. Illumination light beam 120 is directed to polarizer 104B. Although, as depicted, illumination light directed to polarizer 104B comes from illumination source 102B, in general, light from any of the illumination sources of system 100 may be combined to generate an illumination light beam directed to polarizer 104B. In this manner, the spectral components of the illumination light of the small angle RPRC SE subsystem can be configured as a combination of light emitted from multiple illumination sources.

Polarizer 104B is configured to selectively rotate a polarizing element about the optical axis of the illumination light beam 120. In general, polarizer 104B may include any polarizing element and system to rotate the polarizing element known in the art. For example, the polarizer 104B may include a polarizing element mechanically coupled to a rotational actuator. In one example, the polarizing element may be a Rochon prism. In another example, the polarizing element may include a beam displacer. Polarizer 104B is configured to operate within system 100 in either a rotationally active or rotationally inactive state. In one instance, a rotational actuator of polarizer 104B may be inactive such that the polarizing element remains rotationally fixed about the optical axis of illumination light 120. In another instance, the rotational actuator may rotate the polarizing element at a selected angular frequency, $\omega_p$, about the optical axis of the illumination light.

As depicted in FIG. 1, illumination light beam 120 passes through polarizer 104B while the rotational actuator rotates the polarizing element at the selected angular frequency, $\omega_p$. In this manner, polarizer 104B generates a polarized light beam 121. In the depicted embodiment, mirror 105B is a "flip-in" mirror. As such, mirror 105B is attached to an actuation system (not shown) that can be controlled by computing system 130 to selectively remove or insert mirror 105B into the optical path of the polarized light beam 121. During operation of the small angle SE, mirror 105B is removed from the optical path of the polarized light beam 121. Hence, polarized light beam 121 is incident on beamsplitter 106. Beamsplitter 106 directs the polarized light beam 121 towards an objective 101. In the depicted embodiment, the optical surfaces of objective 101 are all reflective. An all-reflective objective allows for a large numerical aperture. This enables a relatively high degree of angular resolution over the range of angles of incidence, particularly for small angles of incidence. In addition, an all-reflective objective efficiently focuses light over a broad spectral range, including small wavelength light (e.g., wavelengths less than 266 nm) that may be substantially absorbed by transmissive optical elements.

In the embodiment depicted in FIG. 1, the all-reflective objective 101 is a Schwartzschild type objective. The Schwartzschild objective depicted in FIG. 1 includes a concave mirror 108 with an opening (e.g., hole) aligned with the optical axis, OA, to allow light to pass in and out of the objective 101. Incoming light passes through the opening, and reflects off convex mirror 107 toward concave mirror 108. The reflected light is focused on the surface of wafer 112 by concave mirror 108. The polarized light beam 121 is focused onto the surface of wafer 112 over a range of angles of incidence by objective 101. As depicted in FIG. 1, an angle of incidence (e.g., angle of incidence, θ) is measured from the optical axis, OA, of the objective 101. The polarized light beam 121 of small angle SE system 100 is focused onto the surface of wafer 112 over a range of angles of incidence by objective 101. In some examples, polarized light beam 121 is focused onto the surface of wafer 112 within a range of angles of incidence between 10 and 50 degrees. In some other examples, polarized light beam 121 is focused onto the surface of wafer 112 within a range of angles of incidence between 10 and 40 degrees. In some examples, a portion of polarized light beam 121 is focused onto the surface of wafer 112 at an angle of incidence less than 20 degrees. In some other examples, a portion of polarized light beam 121 is focused onto the surface of wafer 112 at an angle of incidence less than 15 degrees. Focusing polarized light beam 121 onto the surface of wafer 112 at small angles of incidence results in a small illumination spot. In some examples, the resulting illumination spot is less than 20 micrometers in diameter. In some other examples, the resulting illumination spot size is less than 10 micrometers in diameter.

The interaction of the focused, polarized light beam 121 with wafer 112 modifies the polarization of the radiation by any of reflection, scattering, diffraction, transmission, or other types of processes. After interaction with the wafer 112, modified light 122 is collected by objective 101 over a range of collection angles measured from the optical axis, OA, of the objective 101. Analogous to the incident light, modified light 122 is collected within a range of collection angles between 10 and 50 degrees. In some other examples, modified light 122 is collected from the surface of wafer 112 within a range of collection angles between 10 and 40 degrees. In some examples, a portion of modified light 122 is collected from the surface of wafer 112 at a collection angle less than 20 degrees. In some other examples, a portion of modified light 122 is collected from the surface of wafer 112 at a collection angle less than 15 degrees.

Light from wafer 112 is collected by concave mirror 108 and focused onto convex mirror 107 where it is collimated and exits the Schwartzschild objective through the same hole as the incoming light toward beamsplitter 106. Beamsplitter 106 is configured to pass modified light 122 to compensator 109. In the embodiment depicted in FIG. 1, compensator 109 is configured to selectively rotate a compensator element (e.g., waveplate) about the optical axis of the modified light beam 122. In general, compensator 109 may include any compensator element and system to rotate the compensator element known in the art. For example, the compensator 109 may include a compensator element mechanically coupled to a rotational actuator. Compensator 109 is configured to operate within system 100 in either a rotationally active or rotationally inactive state. In one instance, a rotational actuator of compensator 109 may be inactive such that the compensator element remains rotationally fixed about the optical axis of modified light beam 122. In another instance, the rotational actuator may rotate the compensator element at a selected angular frequency, $\omega_c$, about the optical axis of the modified light beam 122.

As depicted in FIG. 1, modified light beam 122 passes through compensator 109 while the rotational actuator rotates the compensator element at the selected angular frequency, $\omega_c$. The resulting compensated light beam is directed through another polarizer 110. Within the context of SE, polarizer 110 is often referred to as an analyzer. In the depicted embodiment, analyzer 110 is maintained at a fixed angle while the compensated light beam passes through the analyzer 110 and beam focusing optics 111 to spectrometer 112. In spectrometer 112, the beam components having different wavelengths are refracted (e.g., in a prism spectrometer) or diffracted (e.g., in a grating spectrometer) in different directions to different detectors. The detectors may be a linear array of photodiodes, with each photodiode measuring radiation in a different wavelength range. The radiation received by the spectrometer 112 is analyzed with regard to polarization state, allowing for spectral analysis by the spectrometer of radiation passed by the analyzer 110. These spectra 128 are passed to computing system 130 for analysis of the structural characteristics of wafer 112.

One approach to improve measurement sensitivity is to measure more spectral properties related to the geometric and material structure of the sample. For example, in a rotating polarizer spectroscopic ellipsometer (RPSE) system, the polarizer is rotated with an angular frequency, $\omega_p$. The detected signal includes three harmonic terms: the zero frequency (i.e., DC) term, and terms related to $\cos 2\omega_p t$ and $\sin 2\omega_p t$, respectively. In practice, the zero frequency term is used to normalize the $\cos 2\omega_p t$ and $\sin 2\omega_p t$ harmonics, resulting in the [$\alpha$, $\beta$] spectra commonly referenced in the field of ellipsometry. Within the context of a Mueller Matrix formulation, a RPSE system can measure two sets of combinations of Mueller elements, normalized by the first Mueller element (e.g., M00). In a rotating compensator spectroscopic ellipsometer (RCSE) system, the compensator is rotated with an angular frequency, $\omega_c$, and can measure three normalized harmonics. Within the context of a Mueller Matrix formulation, a RCSE system can measure three combinations of Mueller elements normalized by the first Mueller element (M00).

To further improve measurement sensitivity, an SE system may be configured to measure more Mueller elements. Some SE systems employing two rotating polarizing elements are able to measure up to 25 harmonic coefficients corresponding to certain linear combinations of the rotation frequencies of the two rotating polarizing elements. As a result, all 15 normalized Mueller elements can be resolved and thus measured. SE systems that are able to resolve all of the normalized Mueller elements may be referred to as a complete Mueller Matrix spectroscopic ellipsometry (MMSE) system.

In one further aspect, small angle SE system 100 is configured to operate as a complete MMSE system. In a complete MMSE operation mode, polarizer 104B is in the illumination path rotating at an angular frequency, $\omega_p$, and the compensator 109 is in the collection path rotating at an angular frequency, $\omega_c$. The detected signal for the RPRC SE operating in a complete MMSE mode can be expressed in terms of a linear combination of harmonics of both the polarizer and compensator angular frequencies as illustrated in equation (1).

$$S_D = S_F \begin{bmatrix} f_0 + f_1\cos 2\omega_p t + f_2\sin 2\omega_p t + f_3\cos 2\omega_c t + f_4\sin 2\omega_c t + \\ f_5\cos 2(\omega_p - \omega_c)t + f_6\sin(2\omega_p - 2\omega_c)t + \\ f_7\cos 2(\omega_p + \omega_c)t + f_8\sin 2(\omega_p + \omega_c)t + f_9\cos 4\omega_c t + \\ f_{10}\sin 4\omega_c t + f_{11}\cos(2\omega_p - 4\omega_c)t + f_{12}\sin(2\omega_p - 4\omega_c)t + \\ f_{13}\cos(2\omega_p + 4\omega_c)t + f_{14}\sin(2\omega_p + 4\omega_c)t \end{bmatrix} \quad (1)$$

The harmonic coefficients are related to system and sample parameters by equation (2).

$$S_F = \frac{I_i}{4} \quad (2)$$

$$f_0 = \frac{1-p}{2}M_{00} + \frac{1+p}{2}f_{p0}$$

-continued $$f_1 = \frac{1-p}{2}M_{01} + \frac{1+p}{2}f_{p1}$$

$$f_2 = -\frac{1-p}{2}M_{02} + \frac{1+p}{2}f_{p2}$$

$$f_3 = -rM_{30}\sin 2A + s(M_{10} + M_{00}\cos 2A)$$

$$f_4 = rM_{30}\cos 2A - s(M_{20} - M_{00}\sin 2A)$$

$$f_5 = \frac{-r(M_{31}\sin 2A + M_{32}\cos 2A) + s(M_{11} + M_{22} + M_{01}\cos 2A - M_{02}\sin 2A)}{2}$$

$$f_6 = \frac{r(M_{32}\sin 2A - M_{31}\cos 2A) - s(M_{12} - M_{21} + M_{01}\sin 2A + M_{02}\cos 2A)}{2}$$

$$f_7 = \frac{-r(M_{31}\sin 2A - M_{32}\cos 2A) + s(M_{11} - M_{22} + M_{01}\cos 2A + M_{02}\sin 2A)}{2}$$

$$f_8 = \frac{r(M_{32}\sin 2A + M_{31}\cos 2A) - s(M_{12} + M_{21} - M_{01}\sin 2A + M_{02}\cos 2A)}{2}$$

$$f_9 = \frac{1-p}{2}(M_{10}\cos 2A + M_{20}\sin 2A)$$

$$f_{10} = \frac{1-p}{2}(M_{10}\sin 2A - M_{20}\cos 2A)$$

$$f_{11} = \frac{1-p}{4}[(M_{11} + M_{22})\cos 2A - (M_{12} - M_{21})\sin 2A]$$

$$f_{12} = -\frac{1-p}{4}[(M_{12} - M_{21})\cos 2A + (M_{11} + M_{22})\sin 2A]$$

$$f_{13} = \frac{1-p}{4}[(M_{11} - M_{22})\cos 2A + (M_{12} + M_{21})\sin 2A]$$

$$f_{14} = -\frac{1-p}{4}[(M_{12} + M_{21})\cos 2A - (M_{11} - M_{22})\sin 2A]$$

$S_F$ is referred to as the "scale factor" which is proportional to $I_i$, the intensity of the incidence light beam. A is the fixed analyzer angle.

It is recognized herein that in addition to measuring certain off-diagonal Mueller elements, the RPRC MMSE configuration is also capable of improved system calibration using additional system parameters. One group of critical system parameters includes the polarization properties of the compensator (i.e., waveplate) 109. Traditionally, the waveplate 109 is considered "ideal," whereby only the polarizing phase (retardation, $\Gamma$) is used to characterize the waveplate. In practice, however, proper characterization of the waveplate requires quantification of the "diattenuation" or "dichroism." In this regard, retardation of the waveplate, $\Gamma$, is related to its polarizing transmission coefficients ($t_p$, $t_s$) by equation (3).

$$e^{j\Gamma} = \tau = \frac{t_p}{t_s} \quad (3)$$

Equivalently, the waveplate may be described using the three coefficients (s, p, r) of Equation (2) based on the equation (4).

$$s = \frac{1 - |\tau|^2}{1 + |\tau|^2} << 1 \quad (4)$$

$$p = \frac{2|\tau|\cos\Gamma}{1 + |\tau|^2}$$

-continued $$r = \frac{2|\tau|\sin\Gamma}{1+|\tau|^2}$$

Although the embodiment of small angle SE system 100 depicted in FIG. 1 is presented as a RPRC SE system configured to operate in a complete Mueller Matrix mode, in general, other embodiments of a small angle SE system may be contemplated that can be configured to operate in a complete Mueller Matrix mode. Exemplary methods and systems for complete Mueller Matrix SE based on a dual-rotating compensator spectroscopic ellipsometry (DRCSE) architecture are described in U.S. Pat. No. 6,734,968 assigned to KLA-Tencor Corporation, the entirety of which is incorporated herein by reference. The DRCSE architecture disclosed in U.S. Pat. No. 6,734,968 includes a light source, a fixed polarizer, a first rotating waveplate in the illumination path, a second rotating waveplate in the collection path, a fixed analyzer, and a detector. This system is capable of collecting up to 25 harmonic coefficients corresponding to certain linear combinations of the rotation frequencies of the two rotating compensators. As a result, all 15 normalized Mueller elements may be resolved and thus measured. Other SE systems incorporating two rotating polarizing elements are described in: 1) P. S. Hauge, "Mueller Matrix Ellipsometry with Imperfect Compensators," Journal of the Optical Society of America A, 68(11), 1519-1528, 1978, which is incorporated herein in its entirety, 2) R. M. A. Azzam, "A Simple Fourier Photopolarimeter With Rotating Polarizer and Analyzer for Measuring Jones and Mueller Matrices," Optics Communications 25(2), 137-140, 1978, which is incorporated herein in its entirety, and 3) M. L. Aleksandrov, et al., "Methods and Apparatus for Complete Ellipsometry (review)," Journal of Applied Spectroscopy, 44(6), 559-578, 1986, which is incorporated herein in its entirety.

The advancement of semiconductor processes not only results in a decrease in the size of critical dimensions, but also an increase in the complexity of the device structures. This increases the number of critical dimensions that must be resolved for a particular measurement target. For example, modern measurement targets may include more than 10, or even 20, critical dimension parameters. As a result, it is growing increasingly difficult to resolve all critical dimension parameters based on a single measurement subsystem.

In another further aspect, small angle CD metrology system 100 also includes a small angle spectroscopic reflectometer (SR) subsystem in addition to the small angle SE subsystem described hereinbefore. In spectroscopic reflectometry, phase information is lost, but magnitude information is preserved, especially for highly reflective structures measured at small angles of incidence. Small angle SR is a preferred complementary subsystem to small angle SE due to its measurement performance at very small angles of incidence. At very small angles of incidence (e.g., angles of incidence less than 30 degrees), the performance of SE may be diminished. However, SR is able to perform adequate measurements of reflective materials over a small spot size (e.g., less than 15 micrometers) at these very small angles of incidence.

The embodiment of small angle CD metrology system 100 depicted in FIG. 1 includes a small angle SR subsystem configured to perform SR measurements over small angles of incidence. The small angle SR subsystem includes polarizer 104A, objective 101, polarizer 114, and spectrometer 116. As depicted in FIG. 1, a light beam from illumination source 102A is collimated by beam forming optics 103A to generate an illumination light beam 123. Illumination light beam 123 is directed to polarizer 104A. Although, as depicted, illumination light directed to polarizer 104A comes from illumination source 102A, in general, light from any of the illumination sources of system 100 may be combined to generate an illumination light beam directed to polarizer 104A. In this manner, the spectral components of the illumination light of the small angle SR subsystem can be configured as a combination of light emitted from multiple illumination sources.

In some embodiments, polarizer 104A is configured to selectively rotate a polarizing element about the optical axis of the illumination light beam 123. In general, polarizer 104A may include any polarizing element and system to rotate the polarizing element known in the art. For example, the polarizer 104A may include a polarizing element mechanically coupled to a rotational actuator. In one example, the polarizing element may be a Rochon prism. In another example, the polarizing element may include a beam displacer. Polarizer 104A is configured to operate within system 100 in either a rotationally active or rotationally inactive state. In one instance, a rotational actuator of polarizer 104A may be inactive such that the polarizing element remains rotationally fixed about the optical axis of illumination light 123. In another instance, the rotational actuator may rotate the polarizing element at a selected angular frequency, $\omega_p$, about the optical axis of the illumination light.

In some other embodiments, polarizer 104A is configured with a fixed polarization angle about the optical axis of the illumination light beam 123.

As depicted in FIG. 1, illumination light beam 123 passes through polarizer 104A while the rotational actuator rotates the polarizing element at the selected angular frequency, $\omega_p$. In this manner, polarizer 104A generates a polarized light beam 124 directed toward beamsplitter 105A. Beamsplitter 105A is configured to reflect polarized light beam 124 toward mirror 105B. As discussed hereinbefore, mirror 105B is a "flip-in" mirror. As such, mirror 105B is attached to an actuation system (not shown) that can be controlled by computing system 130 to selectively remove or insert mirror 105B into the optical path of the polarized light beam 121. During operation of the small angle SR subsystem, mirror 105B is inserted into the optical path of the polarized light beam 124. Hence, polarized light beam 124 is incident on mirror 105B which redirects polarized light beam 124 toward beamsplitter 106. Beamsplitter 106 directs the polarized light beam 124 towards objective 101. The polarized light beam 124 is focused onto the surface of wafer 112 over a range of angles of incidence by objective 101. The polarized light beam 124 of the small angle SR subsystem is focused onto the surface of wafer 112 over a range of angles of incidence by objective 101. In some examples, polarized light beam 124 is focused onto the surface of wafer 112 within a range of angles of incidence between 10 and 50 degrees. In some other examples, polarized light beam 124 is focused onto the surface of wafer 112 within a range of angles of incidence between 10 and 40 degrees. In some examples, a portion of polarized light beam 124 is focused onto the surface of wafer 112 at an angle of incidence less than 20 degrees. In some other examples, a portion of polarized light beam 124 is focused onto the surface of wafer 112 at an angle of incidence less than 15 degrees. Focusing polarized light beam 124 onto the surface of wafer 112 at small angles of incidence results in a small illumination spot.

In some examples, the resulting illumination spot is less than 20 micrometers in diameter. In some other examples, the resulting illumination spot size is less than 10 micrometers in diameter.

The interaction of the focused, polarized light beam 124 with wafer 112 modifies the polarization of the radiation by any of reflection, scattering, diffraction, transmission, or other types of processes. After interaction with the wafer 112, modified light 125 is collected by objective 101 and directed to beamsplitter 106. Beamsplitter 106 is configured to reflect modified light 125 to mirror 105B. Modified light 125 is reflected by mirror 105B to beamsplitter 105A. Beamsplitter 105A is configured to transmit modified light 125 toward mirror 113. Mirror 113 redirects modified light 125 toward polarizer 114. In the embodiment depicted in FIG. 1, polarizer 114 includes a polarizer element that remains rotationally fixed about the optical axis of modified light beam 125 while the modified light beam 125 passes through the polarizer 114 and beam focusing optics 115 to spectrometer 116. In spectrometer 116, the beam components having different wavelengths are refracted (e.g., in a prism spectrometer) or diffracted (e.g., in a grating spectrometer) in different directions to different detectors. The detectors may be a linear array of photodiodes, with each photodiode measuring radiation in a different wavelength range. The radiation received by the spectrometer 116 is analyzed with regard to polarization state, allowing for spectral analysis by the spectrometer of radiation passed by the polarizer 114. These spectra 129 are passed to computing system 130 for analysis of the structural characteristics of wafer 112.

In general, reflectometry and ellipsometry are indirect methods of measuring physical properties of the specimen under inspection. In most cases, the measured values cannot be used to directly determine the physical properties of the specimen. The nominal measurement process consists of parameterization of the structure (e.g., film thicknesses, critical dimensions, etc.) and the machine (e.g., wavelengths, angles of incidence, polarization angles, etc.). A model is created that attempts to predict the measured values. In general, the model includes parameters associated with the machine and the specimen.

Machine parameters are parameters used to characterize the metrology system itself (e.g., small angle CD metrology system 100). Exemplary machine parameters include angle of incidence (AOI), analyzer angle ($A_0$), polarizer angle ($P_0$), illumination wavelength, numerical aperture (NA), etc. Specimen parameters are parameters used to characterize the specimen (e.g., wafer 112). For a thin film specimen, exemplary specimen parameters include refractive index, dielectric function tensor, nominal layer thickness of all layers, layer sequence, etc. For measurement purposes, the machine parameters are treated as known, fixed parameters and the specimen parameters are treated as unknown, floating parameters. The floating parameters are resolved by an iterative process (e.g., regression) that produces the best fit between theoretical predictions and experimental data. The unknown specimen parameters are varied and the model output values are calculated until a set of specimen parameter values are determined that results in a close match between the model output values and the experimentally measured values.

As described with reference to small angle CD metrology system 100, measurement spectra 128 are generated by the small angle SE subsystem and measurement spectra 129 are generated by the small angle SR subsystem. In some examples, computer system 130 receives measurement spectra 128 and 129 and determines specimen parameter values based on a combined analysis (e.g., regression) that includes both measurement spectra 128 and 129 and measurement models associated with both the SE and SR measurements. In one example, a regression process (e.g., ordinary least squares regression) is employed to identify specimen parameter values that minimize a cost function that includes the differences between the model output values and the experimentally measured values for both the SE measurements and the SR measurements. In some other examples, computer system 130 receives measurement spectra 128 and 129 and determines specimen parameter values based on a separate analysis (e.g., regression) of the SE and SR measurements. This separate analysis may be preferred when it is clear that one measurement technique delivers superior measurement results for a particular measurement application.

In another further aspect, measurements are performed by the small angle SE subsystem at two orthogonal, or nearly orthogonal azimuth angles. In some embodiments, the small angle SE subsystem described herein is further configured to perform measurements at two different azimuth angles, typically separated by approximately ninety degrees. For some challenging samples, this configuration may result in improved measurement sensitivity. In a preferred embodiment, small angle SE subsystem is operated in a complete MMSE mode during measurements performed over two orthogonal, or nearly orthogonal azimuth angles. In addition, measurements can be taken over two orthogonal, or nearly orthogonal azimuth angles by both the small angle SE subsystem and small angle SR subsystem for combined analysis as described hereinbefore.

The measurement response of a particular structure is strongly related to the orientation (i.e., angle of incidence and azimuth angle) of the incident measurement light beam with respect to the structure. In yet another further aspect, a dynamic aperture subsystem is included in small angle CD metrology system 100 to enable measurements at different angles of incidence and different azimuth angles. The dynamic aperture subsystem is operable to isolate specific ranges of angles of incidence and azimuth for improved measurement sensitivity.

Figure 3:
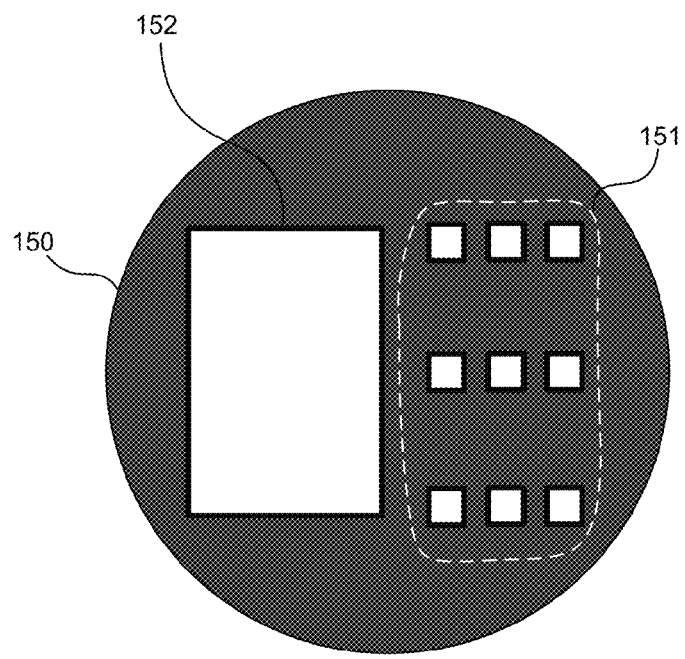
FIG. 3 illustrates a schematic view of a pupil plane 150 within small angle CD metrology system 100 having an illumination aperture 152 and an array of collection apertures 151 in one embodiment.
Figure 4:
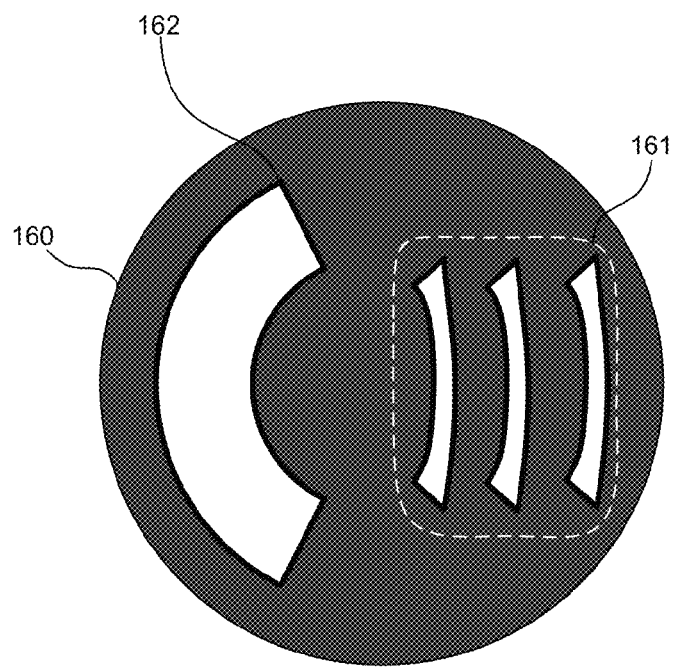
FIG. 4 illustrates a schematic view of a pupil plane 160 within small angle CD metrology system 100 having an illumination aperture 162 and an array of collection apertures 161 in another embodiment.

FIG. 3 illustrates, by way of non-limiting example, an accessible pupil plane 150 within small angle CD metrology system 100. At the illustrated pupil plane 150, an illumination aperture 152 and an array of collection apertures 151 are visible. Light passed through collection apertures in the same row (horizontally aligned in FIG. 3) is associated with substantially similar azimuth angles, while light passed through collection apertures in the same column (vertically aligned in FIG. 3) is associated with substantially similar angles of incidence. FIG. 4 illustrates an accessible pupil plane 160 within small angle CD metrology system 100 in another non-limiting example. At the illustrated pupil plane 160, an illumination aperture 162 and an array of collection apertures 161 are visible. Each collection aperture of array 161 passes light associated with substantially similar angles of incidence over a range of azimuth angles. Hence, each different collection aperture of the array 161 passes light associated with a different angle of incidence.

In some embodiments, the dynamic aperture subsystem includes a shutter system (not shown) controlled by a controller (e.g., computing system 130) to selectively pass light through particular areas (such as the areas described with reference to FIGS. 3 and 4) in a pupil plane. In this manner, the shutter system controls access to multiple, different angles of incidence and azimuth. In one example, the mechanical shutter system may be configured to selectively pass light through any one of the three rows of collection apertures illustrated in FIG. 3. In this manner, measurements are isolated to a particular azimuth angle, or very small range of azimuth angle. In another example, the mechanical shutter system may be configured to selectively pass light through any one of the collection apertures illustrated in FIG. 4. In this manner, measurements are isolated to a particular angle of incidence, or very small range of angles of incidence. After the shutter selects the desired combination of angles of incidence and azimuth, the spectrometer (e.g., spectrometer 112 or 116) detects the collected light associated with the selection. Access to multiple, different angles may be performed sequentially.

In yet another example, multiple angles (e.g., three different angles) are selected at the same time, and the light beams passed through the aperture are shifted into different portions of the entrance of the spectrometer. In this manner, the spectrometer detects the collected light associated with different angles, simultaneously.

Figure 5:
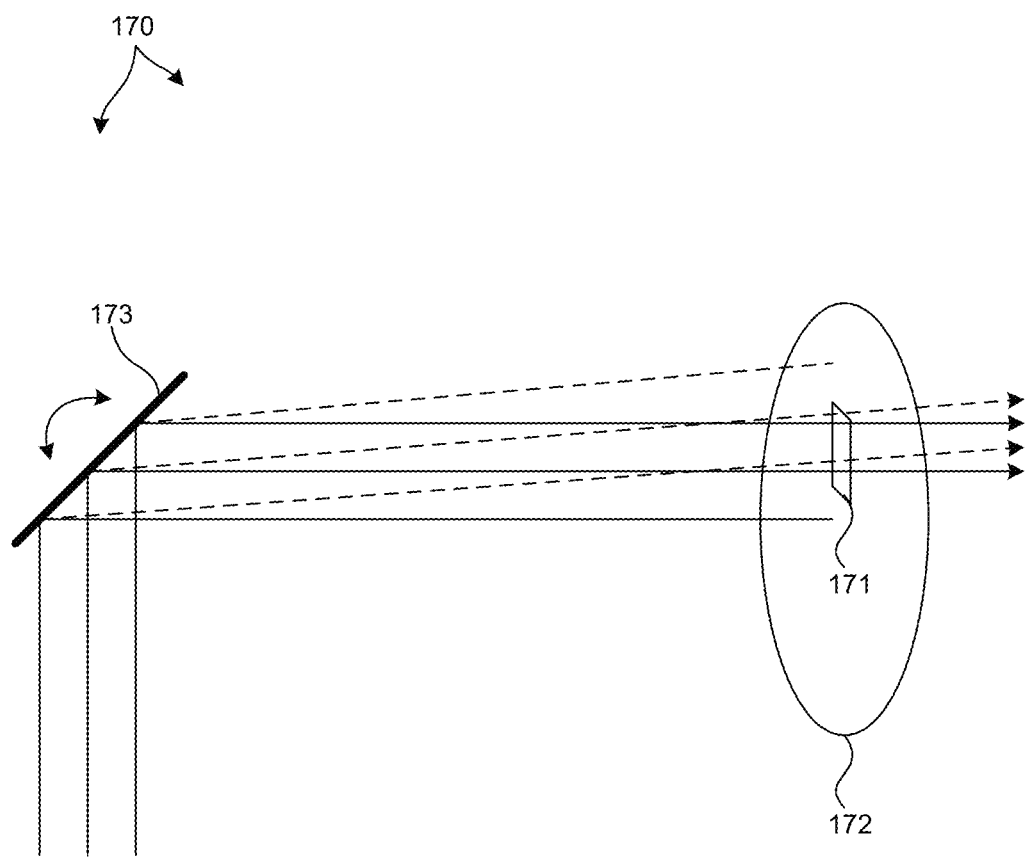
FIG. 5 illustrates a dynamic aperture subsystem 170 in one embodiment.

FIG. 5 illustrates a dynamic aperture subsystem 170 in yet another embodiment. Dynamic aperture subsystem 170 includes one or more actuated mirrors 173 (e.g., micro electro mechanical system (MEMS) actuated mirror, galvanometer actuated mirror, Lorentz coil actuated mirror, etc.). The actuated mirror 173 is controlled by a controller (e.g., computing system 130) to direct a beam of measurement light (i.e., either illumination light or collection light) at selectively different angles toward a fixed aperture 171 in the light path of the measurement light beam. In this manner, the measurement light beam is incident to the fixed aperture 171 at different locations in the pupil plane 172. Hence, selectively different portions of the measurement beam are passed through the fixed aperture 171. As illustrated in FIG. 5, in a first instance, a portion of the light beam passes through the fixed aperture 171 (depicted as the set of solid lines passing through aperture 171). After the actuated mirror 173 is rotated, in a second instance, a different portion of the light beam passes through the fixed aperture 171 (depicted as the set of dashed lines passing through aperture 171). In some examples, the fixed aperture is designed to pass a narrow range of angles of incidence over a broader range of azimuth angles. In some other examples, the fixed aperture is designed to pass a narrow range of azimuth angles over a broader range of angles of incidence. In some other examples, the fixed aperture is designed to pass only a narrow range of azimuth angles and a narrow range of angles of incidence.

In some other embodiments, multiple spectrometers (e.g., three spectrometers) are employed to simultaneously detect signals corresponding to multiple different angles of incidence and/or azimuth.

A dynamic aperture subsystem as described herein may be located at a variety of different pupil locations within a small angle CD metrology system. With reference to small angle CD metrology system 100 depicted in FIG. 1, a dynamic aperture subsystem may be located in the illumination path (i.e., between the illumination source and objective 101). Alternatively, or in combination with another dynamic aperture subsystem, a dynamic aperture subsystem may be located in the collection path (i.e., between beamsplitter 106 and spectrometer 112 for the small angle SE subsystem or between beamsplitter 105A and spectrometer 116 for the small angle SR subsystem). Alternatively, or in combination, a dynamic aperture subsystem may be located in the common path (i.e., between objective 101 and beamsplitter 106 for the small angle SE subsystem or between objective 101 and beamsplitter 105A for the small angle SR subsystem).

In a preferred embodiment, any dynamic aperture subsystem is located in either or both the illumination path and the collection path, and not in the common path. However, in some embodiments, a dynamic aperture subsystem may be located in the common path.

In a further preferred embodiment, full illumination is provided to the wafer 112 and any dynamic aperture subsystem is located in the collection path. However, in some embodiments, a dynamic aperture subsystem may be located in the illumination path and full collection light is provided to the spectrometer.

In general, different dynamic aperture subsystems may be employed as part of the small angle SE subsystem and the small angle SR subsystem, or the same dynamic aperture subsystem may be employed during operation of either subsystem.

Figure 2:
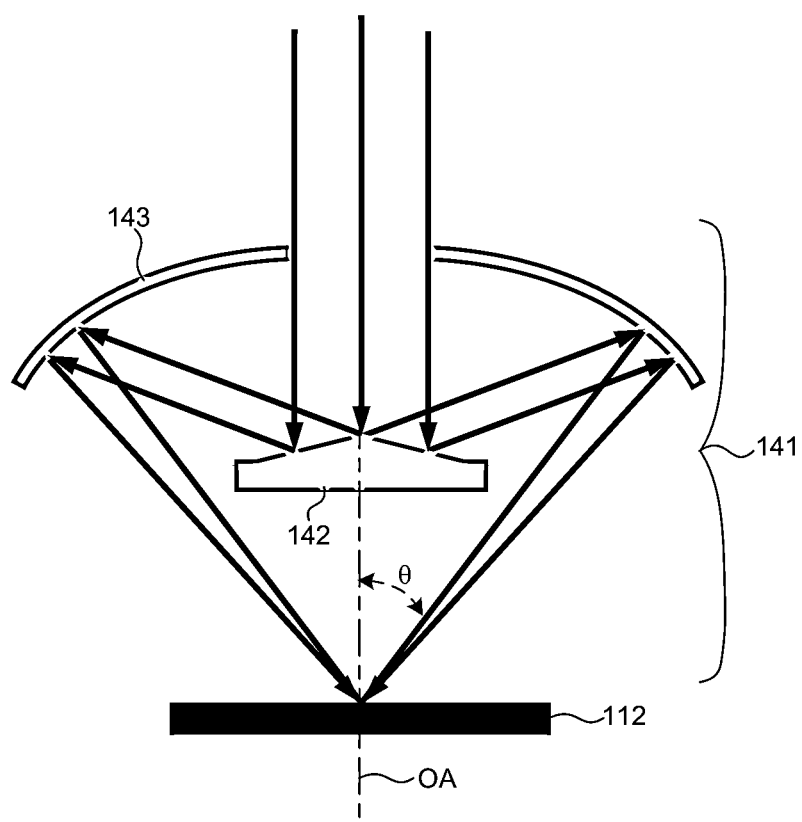
FIG. 2 illustrates a schematic view of a Schwartzschild type objective 141 suitable for use in small angle CD metrology system 100.

As discussed hereinbefore, the configuration of the SE and SR subsystems for operation at small angles of incidence directly results in a small measurement spot. In yet another further aspect, the size of the measurement spot may be further reduced by replacing the convex mirror 107 in the Schwarzschild objective 101 depicted in FIG. 1 by an axicon mirror element. FIG. 2 illustrates a schematic view of a Schwartzschild type objective 141 suitable for use in a small angle CD metrology system in another embodiment. The Schwartzschild objective 141 depicted in FIG. 2 includes a concave mirror 143 with an opening (e.g., hole) aligned with the optical axis, OA, to allow light to pass in and out of the objective 141. Incoming light passes through the opening, and reflects off axicon mirror 142 toward concave mirror 143. The reflected light is focused on the surface of wafer 112 by concave mirror 143. The use of an axicon mirror element allows a relatively long depth of focus, and improved collimation of the beam reflected from the axicon mirror. In some embodiments, the axicon mirror 142 may be translated along the optical axis, OA, to change the angle of incidence on the surface of wafer 112. Calculations of the intensity distribution of the focal point at the wafer surface have demonstrated that it is possible to achieve a spot size of less than 10 microns diameter using an axicon mirror element as described with reference to FIG. 2.

In some embodiments, the spot size may be further reduced by employing additional beam shaping elements. For example, one or more apodizers placed at appropriate positions in the illumination light path, collection light path, or both, may be used to reduce the spot size. However, the use of apodizers to reduce spot size may not be preferred due to the loss of light associated with their use. This may be of particular concern in light starved applications (e.g., applications with low signal to noise ratio or high throughput applications).

Figure 7:
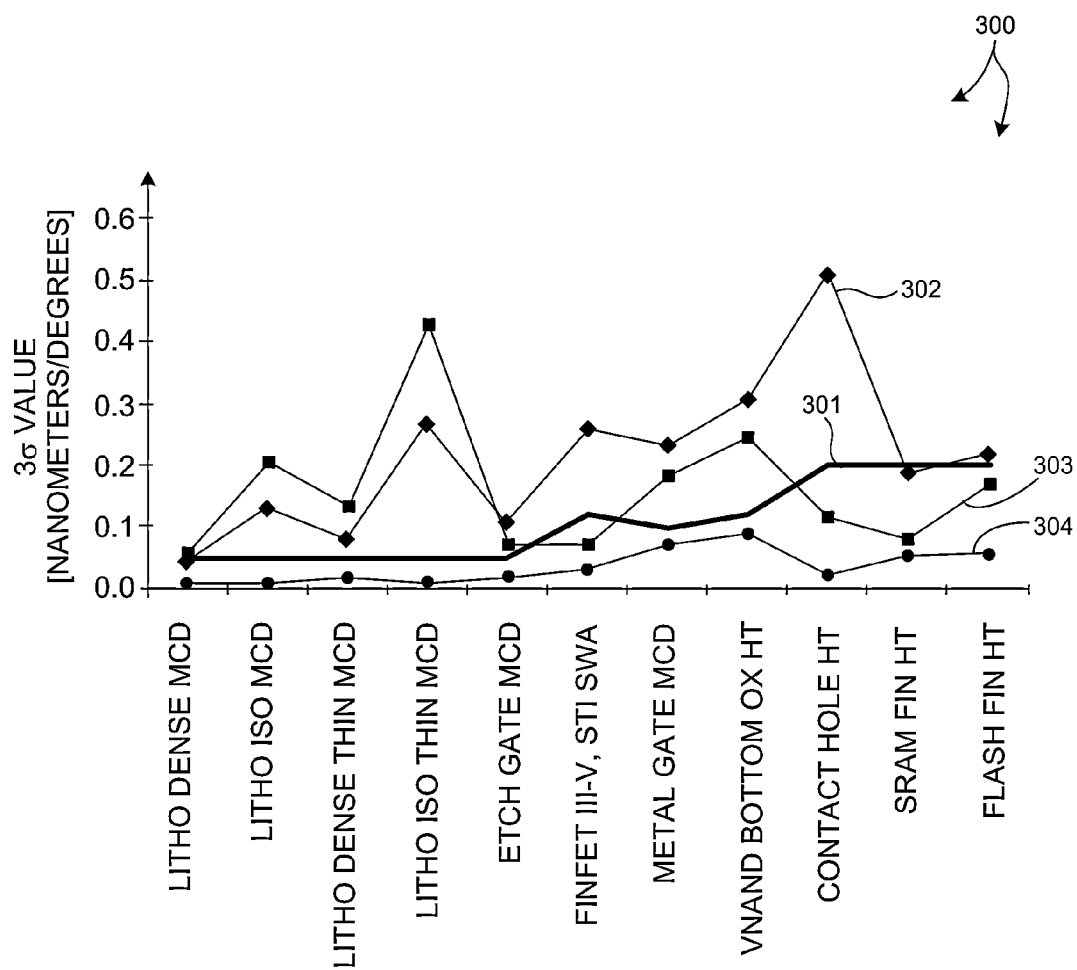
FIG. 7 illustrates a plot 300 of simulation results of the measurement precision of several different metrology systems for comparison.

In a preferred embodiment, small angle CD metrology system 100 combines a small angle SE subsystem operating in a complete Mueller Matrix mode and a small angle SR subsystem as described herein. The combination enables small measurement spot size and high measurement speed. FIG. 7 illustrates a plot 300 of simulation results of the measurement precision of several different metrology systems for comparison. The results are simulations of measurements performed on a set of challenging samples. The samples include lithography samples, etch samples at the 11 nm technology node, FinFET structures formed with III-V materials, very deep VNAND structures with more than 60 film stacks, complex SRAM structures, and Flash FinFET structures at the 14 nm node. As illustrated in FIG. 7, the measurements include middle critical dimension (MCD) measurements, side wall angle (SWA) measurements, and height (HT) measurements. Plotline 301 illustrates the measurement precision requirement associated with each measurement. Plotline 302 illustrates the simulated performance of a traditional SE system (e.g., RPSE system). Plotline 303 illustrates the simulated performance of traditional SR system. Plotline 304 illustrates the simulated performance of a small angle CD metrology system 100 that combines a small angle SE subsystem operating in a complete Mueller Matrix mode and a small angle SR subsystem as described herein. As illustrated, the small angle CD metrology system combining a small angle SE subsystem operating in a complete Mueller Matrix mode and a small angle SR subsystem performs significantly better than traditional SE and SR systems and is able to meet challenging measurement system requirements.

Figure 8:
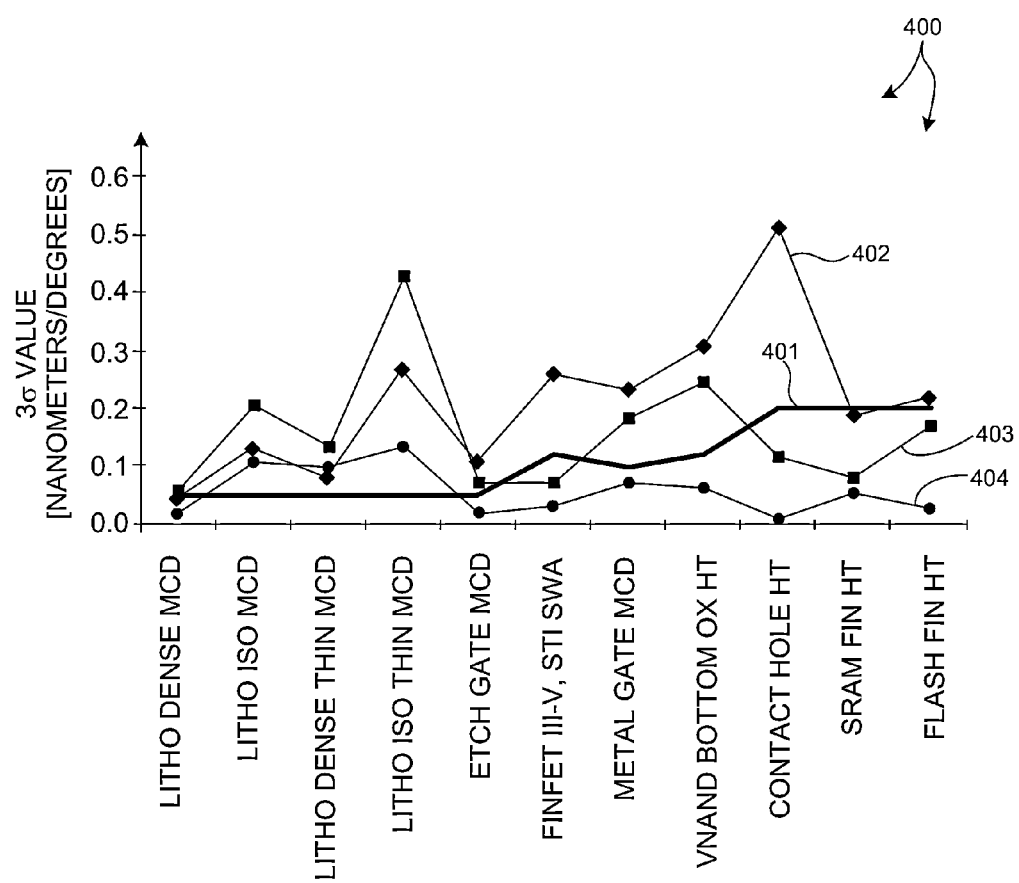
FIG. 8 illustrates a plot 400 of simulation results of the measurement precision of several different metrology systems for comparison.

In another embodiment, a small angle CD metrology system includes a small angle SE subsystem operating in a complete Mueller Matrix mode with measurement data collected over two orthogonal azimuth angles (e.g., 0 degrees and 90 degrees). FIG. 8 illustrates a plot 400 of simulation results of the measurement precision of several different metrology systems for comparison. The results are simulations of measurements performed on the same set of challenging samples described with reference to FIG. 7. Plotline 401 illustrates the measurement precision requirement associated with each measurement. Plotline 402 illustrates the simulated performance of a traditional SE system (e.g., RPSE system). Plotline 403 illustrates the simulated performance of traditional SR system. Plotline 404 illustrates the simulated performance of a small angle CD metrology system including a small angle SE subsystem operating in a complete Mueller Matrix mode with measurement data collected over two orthogonal azimuth angles (e.g., 0 degrees and 90 degrees) as described herein. As illustrated, the small angle SE subsystem operating in a complete Mueller Matrix mode with measurement data collected over two orthogonal azimuth angles performs significantly better than traditional SE and SR systems for many challenging measurements and is able to meet some measurement system requirements.

In a further embodiment, small angle CD metrology system 100 may include one or more computing systems 130 employed to perform CD measurements over small angles of incidence as described herein. In particular, one or more computing systems 130 may be employed to perform CD measurement analysis, perform dynamic aperture selection functionality, and control various parameters of the CD measurement (e.g., rotational frequency of polarizers, etc.). The one or more computing systems 130 may be communicatively coupled to spectrometers 102 and 116. In one aspect, the one or more computing systems 130 are configured to receive measurement data 128 and 129 associated with a critical dimension measurement of the specimen 112. In one example, the measurement data 128 and 129 includes an indication of the measured spectral response of the specimen based on the one or more sampling processes from the spectrometers 112 and 116, respectively. The one or more computer systems 130 are further configured to determine a value of at least one CD parameter value associated with the specimen 112.

In a further embodiment, the one or more computing systems 130 are configured to access model parameters in real-time, employing Real Time Critical Dimensioning (RTCD), or access libraries of pre-computed models for determining a value of at least one CD parameter value associated with the specimen 112. In summary, some form of CD-engine may be used to evaluate the difference between assigned CD parameters of a specimen and CD parameters for the same specimen as returned by the measurement system.

It should be recognized that the various steps described throughout the present disclosure may be carried out by a single computer system 130 or, alternatively, a multiple computer system 130. Moreover, different subsystems of the system 100, such as the small angle SE subsystem or the small angle SR subsystem, may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometers 112 and 116, any of the illumination sources 102A and 102B, any dynamic aperture subsystem, or any other element of the small angle CD metrology system 100 in any manner known in the art. For example, the one or more computing systems 130 may be coupled to a computing system of the spectrometer 112, a computing system of the illumination source 102A, or a computing system of the dynamic aperture subsystem 170. In another example, the spectrometer 104, illuminator 102A, and dynamic aperture subsystem 170 may be controlled by a single computer system. In this manner, the computer system 130 of the system 100 may be coupled to a single computer system.

The computer system 130 of the system 100 may be configured to receive and/or acquire data or information from the subsystems of the system (e.g., spectrometers 112 and 116, illuminators 102A and 102B, a dynamic aperture subsystem, and the like) by a transmission medium that may include wireline and/or wireless portions. In this manner, the transmission medium may serve as a data link between the computer system 130 and other subsystems of the system 100. Further, the computing system 130 may be configured to receive measurement data via a storage medium (i.e., memory). For instance, the spectral results obtained using a spectrometer of any of the small angle SE subsystem and the small angle SR subsystem may be stored in a permanent or semi-permanent memory device (e.g., memory 132).

Moreover, the computer system 130 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 130 and external systems.

The computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods and functionality such as those described herein may be stored in memory 132 and transmitted over a carrier medium (e.g., bus 133) to processor 132 for execution. The carrier medium may be a transmission medium such as a wire, cable, or wireless transmission link. The carrier medium may also include a computer-readable medium such as a read-only memory, a random access memory, a magnetic or optical disk, or a magnetic tape.

In some examples, computing system 130 is programmed to generate control signals to control the angular orientation or the angular frequency of any of the rotating optical elements of system 100 (e.g., polarizers 104A and 104B, compensator 109, analyzer 110, polarizer 114, etc.). Computing system 130 may also receive data indicative of the angular orientation or angular frequency of any of the rotating optical elements of system 100.

In some other examples, computing system 130 is programmed to generate control signals to control the position of other elements in the optical path (e.g., "flip-in" mirror 105B, a shutter or movable mirror in a dynamic aperture subsystem, and other beam shaping and focusing optics). Computing system 130 may also receive data indicative of the position of these elements.

In another example, computing system 130 is programmed to generate control signals to a wafer positioning system (not shown) to control the position of wafer 112 with respect to the optical subsystems.

Figure 6:
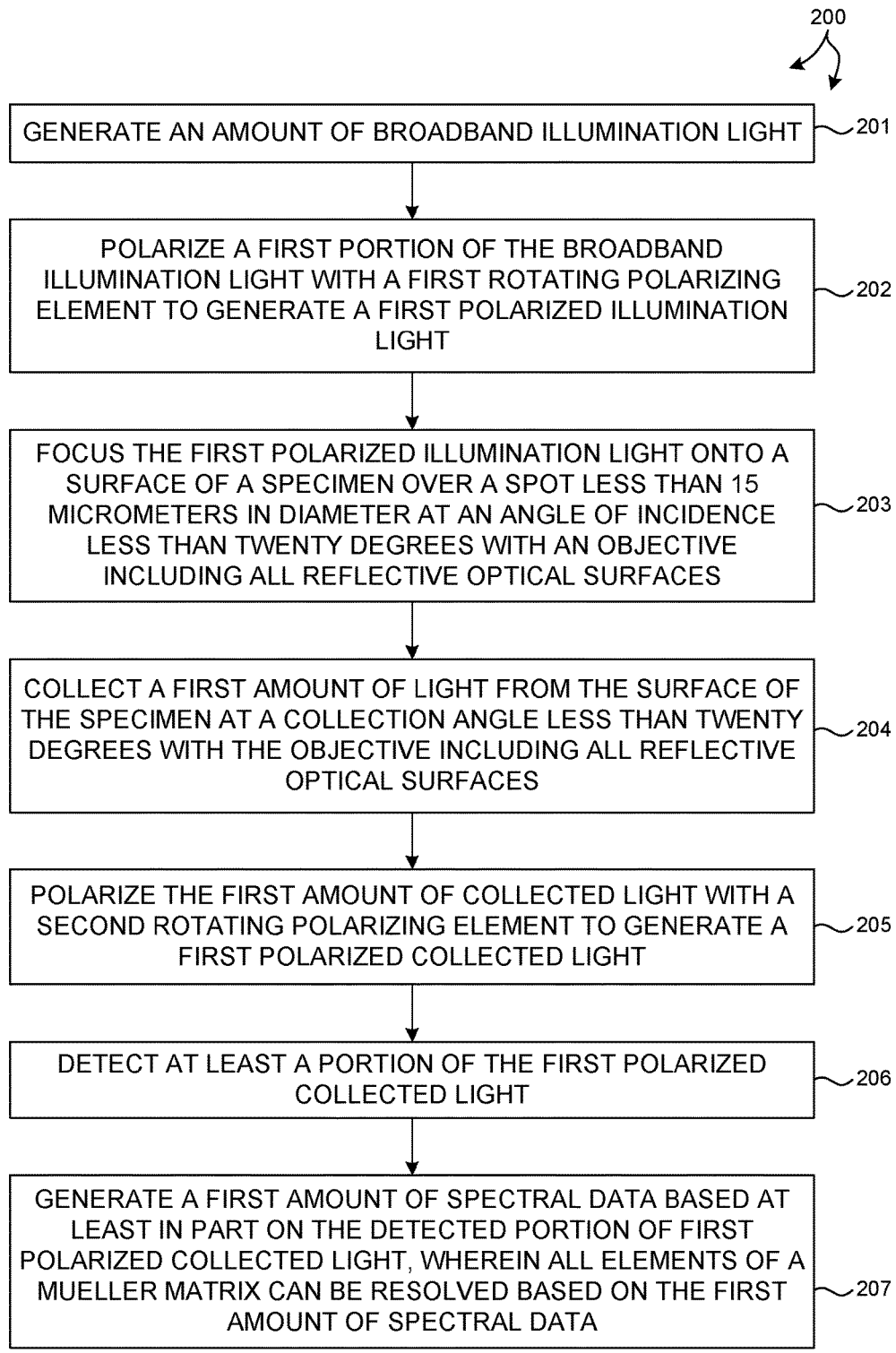
FIG. 6 is a flowchart illustrative of an exemplary method 200 of measurement of structural characteristics of a semiconductor wafer over small angles of incidence.

FIG. 6 illustrates a method 200 suitable for implementation by the small angle CD metrology system 100 of the present invention. In one aspect, it is recognized that data processing blocks of method 200 may be carried out via a pre-programmed algorithm executed by one or more processors of computing system 130. While the following description is presented in the context of system 100, it is recognized herein that the particular structural aspects of inspection system 100 do not represent limitations and should be interpreted as illustrative only.

In block 201, one or more illumination sources generate an amount of broadband illumination light.

In block 202, a first portion of the broadband illumination light is polarized with a first rotating polarizing element to generate a first polarized illumination light.

In block 203, the first polarized illumination light is focused onto a surface of a specimen over a spot less than 15 micrometers in diameter at an angle of incidence less than twenty degrees with an objective including all reflective optical surfaces.

In block 204, a first amount of light from the surface of the specimen is collected at an angle of collection less than twenty degrees with the objective including all reflective optical surfaces.

In block 205, the first amount of collected light is polarized with a second rotating polarizing element to generate a first polarized collected light.

In block 206, at least a portion of the first polarized collected light is detected, for example, by a detector included as part of spectrometer 112.

In block 207, a first amount of spectral data is generated based on the detected portion of first polarized collected light, wherein all elements of a Mueller Matrix can be resolved based on the first amount of spectral data.

In addition, method 200 may be extended by polarizing a second portion of the broadband illumination light to generate a second polarized illumination light. The second polarized illumination light is focused onto a surface of a specimen over a spot less than 15 micrometers in diameter at an angle of incidence less than twenty degrees with an objective including all reflective optical surfaces. The second amount of light is collected from the surface of the specimen at an angle of collection less than twenty degrees with the objective. The second amount of collected light is polarized to generate a second polarized collected light. At least a portion of the second polarized collected light is detected, for example, by a detector included as part of spectrometer 116. A second amount of spectral data is generated based on the detected portion of the second polarized collected light. Finally, a parameter value associated with a measurement target on the specimen is determined based on the first and second amounts of spectral data.

It is noted that the measurement data generated by a small angle CD metrology system described herein may be based on more than one measurement subsystem. In fact, a particular measurement application may be configured to employ any combination of available metrology sub-systems within a single tool, or across a number of different tools. In the case of a particular CD or thin-film application, a cost function minimization can be applied sequentially for one sub-system at a time, or it can be applied in parallel, where all sub-systems are represented in a cost-function. The advantages and disadvantages for a parallel vs. sequential optimization may be weighed against each other for a given application. For instance, one may choose a sequential mode, because it is overall faster, or one may use a parallel mode, because it returns an overall better matching result.

A system implementing the methods described herein may be configured in a number of different ways. For example, the system may include any suitable combination of elements to condition light directed to or collected from the specimen (e.g., apodizers, filters, etc.).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

In general, a wafer includes multiple layers. The measurement of the relative positions of these layers is commonly termed an "overlay measurement application." Each layer includes periodic structures, and the relative positions of the layers are measured as a shift in one direction or more directions. Thus, in general, and for purposes of this patent document, overlay measurements are regarded as a CD measurement, where the position shifts of the periodic structures are the CD parameters to be measured.

As described herein, the term "critical dimension application" or "critical dimension measurement application" includes any critical dimension measurement.

As described herein, the term "metrology system" includes any system employed at least in part to characterize a specimen in any aspect. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a site on a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An apparatus comprising:
    a broadband illumination source configured to generate illumination light;
    a small angle spectroscopic ellipsometer subsystem comprising,
        a first polarizer element configured to receive a first portion of the illumination light and generate a first polarized illumination light,
        an objective including all reflective optical surfaces, wherein the objective is configured to focus the first polarized illumination light onto a surface of a specimen at an angle of incidence less than twenty degrees and collect an amount of light from the surface of the specimen at a collection angle less than twenty degrees,
        a second polarizer element configured to receive the amount of collected light and generate an amount of polarized collected light, and
        a first detector configured to detect at least a portion of the polarized collected light;
    a spectroscopic reflectometer subsystem comprising,
        a third polarizer element configured to receive a second portion of the illumination light and generate a second polarized illumination light,
        the objective including all reflective optical surfaces, wherein the objective is configured to focus the second polarized illumination light onto a surface of a specimen at an angle of incidence less than twenty degrees and collect an amount of light from the surface of the specimen at a collection angle less than twenty degrees,
        a fourth polarizer element configured to receive the amount of collected light, and
        a second detector configured to detect at least a portion of the collected light; and
    a moveable mirror element that is moveable from a first location to a second location, wherein the moveable mirror element in the first location causes the first polarized illumination light to propagate toward the objective and not the second polarized illumination light, and wherein the moveable mirror element in the second location causes the second polarized illumination light to propagate toward the objective and not the first polarized illumination light, wherein the moveable mirror element in the first location, the second location, or both, is located in an optical path between the first polarizer element of the small angle spectroscopic ellipsometer subsystem and the objective, in an optical path between the third polarizer element of the spectroscopic reflectometer subsystem and the objective, or both.

2. The apparatus of claim 1, wherein the small angle spectroscopic ellipsometer subsystem is configured to operate in a complete Mueller Matrix mode.

3. The apparatus of claim 1, wherein the objective is a Schwartzschild objective, and wherein the Schwartzschild objective includes an axicon mirror element.

4. The apparatus of claim 1, wherein the small angle spectroscopic ellipsometer subsystem is configured as a rotating polarizer, rotating compensator spectroscopic ellipsometer.

5. The apparatus of claim 1, wherein a first amount of measurement data is determined by the small angle spectroscopic ellipsometer subsystem at a first azimuth angle relative to a measurement target, and wherein a second amount of measurement data is determined by the small angle spectroscopic ellipsometer subsystem at a second azimuth angle relative to the measurement target, wherein the first azimuth angle is approximately orthogonal to the second azimuth angle, and wherein a parameter value associated with the measurement target is determined based on the first and second amounts of measurement data.

6. The apparatus of claim 1, wherein the broadband illumination source is a laser driven plasma light source.

7. The apparatus of claim 1, wherein a first amount of measurement data is determined by the small angle spectroscopic ellipsometer subsystem from a measurement target, and wherein a second amount of measurement data is determined by the small angle spectroscopic reflectometer subsystem from the measurement target, and wherein a parameter value associated with the measurement target is determined based on the first and second amounts of measurement data.

8. The apparatus of claim 1, further comprising:
a dynamic aperture element located in an optical path of the small angle spectroscopic ellipsometer subsystem, wherein the dynamic aperture element is configured to selectively pass light associated with a limited range of angles of incidence or azimuth.

9. The apparatus of claim 8, wherein the dynamic aperture element is located in a collection path of the small angle spectroscopic ellipsometer subsystem.

10. The apparatus of claim 8, wherein the dynamic aperture element is either a mechanical shutter or an actuated mirror.

11. The apparatus of claim 1, further comprising:
a dynamic aperture subsystem configured to selectively pass light through an aperture in an optical path of the small angle spectroscopic ellipsometer subsystem; and
a control system communicatively coupled to the dynamic aperture subsystem, wherein the control system is configured to communicate a control signal to the dynamic aperture subsystem to pass light associated with a reduced range of angles of incidence or azimuth through the aperture.

12. The apparatus of claim 11, wherein the dynamic aperture subsystem is located in a collection path of the small angle spectroscopic ellipsometer subsystem.

13. The apparatus of claim 11, wherein the dynamic aperture subsystem includes either a mechanical shutter or an actuated mirror.

14. A method comprising:
generating an amount of broadband illumination light;
polarizing a first portion of the broadband illumination light with a first polarizing element to generate a first polarized illumination light;
focusing the first polarized illumination light onto a surface of a specimen over a spot less than 15 micrometers in diameter at an angle of incidence less than twenty degrees with an objective including all reflective optical surfaces;
collecting a first amount of light from the surface of the specimen at a collection angle less than twenty degrees with the objective including all reflective optical surfaces;
polarizing the first amount of collected light with a second polarizing element to generate a first polarized collected light;
detecting at least a portion of the first polarized collected light;

polarizing a second portion of the broadband illumination light with a third polarizing element to generate a second polarized illumination light;
focusing the second polarized illumination light onto a surface of a specimen over a spot less than 15 micrometers in diameter at an angle of incidence less than twenty degrees with an objective including all reflective optical surfaces;
collecting a second amount of light from the surface of the specimen at a collection angle less than twenty degrees with the objective including all reflective optical surfaces;
polarizing the second amount of collected light with a fourth polarizing element to generate a second polarized collected light; and
detecting at least a portion of the second polarized collected light; and
locating a moveable mirror element at a first location or a second location, wherein the moveable mirror element in the first location causes the first polarized illumination light to propagate toward the objective and not the second polarized illumination light, and wherein the moveable mirror element in a second location causes the second polarized illumination light to propagate toward the objective and not the first polarized illumination light, wherein the moveable mirror element in the first location, the second location, or both, is located in an optical path between the first polarizer element and the objective, in an optical path between the third polarizer element and the objective, or both.

15. The method of claim 14, wherein the objective is a Schwartzschild objective, and wherein the Schwartzschild objective includes an axicon mirror element.

16. The method of claim 14, further comprising:
determining a second amount of spectral data; and
determining a parameter value associated with the measurement target based on the first and second amounts of spectral data, wherein the first amount of spectral data is associated with light collected from a measurement target on the surface of the specimen at a first azimuth angle relative to the measurement target, and wherein the second amount of spectral data is associated with light collected from the measurement target on the surface of the specimen at a second azimuth angle relative to the measurement target, and wherein the first azimuth angle is approximately orthogonal to the second azimuth angle.

17. The method of claim 14, further comprising:
generating a first amount of spectral data based at least in part on the detected portion of first polarized collected light, wherein all elements of a Mueller Matrix can be resolved based on the first amount of spectral data; and
generating a second amount of spectral data based at least in part on the detected portion of the second polarized collected light.

18. The method of claim 17, further comprising:
determining a parameter value associated with the measurement target based on the first and second amounts of spectral data.

19. The method of claim 14, further comprising:
selectively passing light through an aperture in an optical path of any of the first portion of the broadband illumination light, the first polarized illumination light, the first amount of collected light, and the first polarized collected light, wherein the light passed through the aperture is associated with a reduced range of angles of incidence or azimuth.

\* \* \* \* \*